United States Patent [19]
Brennan

[11] Patent Number: 6,126,627
[45] Date of Patent: Oct. 3, 2000

[54] ADJUSTABLE ANKLE BRACE SYSTEM

[75] Inventor: Frank Brennan, Reading, Pa.

[73] Assignee: X Wraps Designs L.L.C., Reading, Pa.

[21] Appl. No.: 09/005,440

[22] Filed: Jan. 10, 1998

[51] Int. Cl.⁷ ...................................................... A61F 13/00
[52] U.S. Cl. ................................ 602/65; 602/23; 602/27; 602/66
[58] Field of Search .......................... 36/89, 7.1 R, 50.1, 36/140; 602/27–29, 65, 5, 23, 60, 62, 66; D24/190, 192; 128/882

[56] References Cited

U.S. PATENT DOCUMENTS

| | | |
|---|---|---|
| 958,896 | 5/1910 | Shaw . |
| 1,153,977 | 9/1915 | Tweedie . |
| 1,546,551 | 7/1925 | Petri . |
| 1,730,400 | 10/1929 | Wharton . |
| 4,280,488 | 7/1981 | Polsky et al. . |
| 4,313,433 | 2/1982 | Cramer . |
| 4,729,370 | 3/1988 | Kallasy . |
| 4,844,058 | 7/1989 | Vogelbach . |
| 4,878,504 | 11/1989 | Nelson ...................................... 602/27 |
| 4,908,960 | 3/1990 | Hoyt, Jr. . |
| 5,016,623 | 5/1991 | Krahenbuhl . |
| 5,050,620 | 9/1991 | Cooper . |
| 5,067,486 | 11/1991 | Hely . |
| 5,090,404 | 2/1992 | Kallasy . |
| 5,242,379 | 9/1993 | Harris et al. . |
| 5,330,419 | 7/1994 | Toronto et al. . |
| 5,361,517 | 11/1994 | Liener . |
| 5,822,887 | 10/1998 | Turner .......................................... 36/89 |

FOREIGN PATENT DOCUMENTS

| | | |
|---|---|---|
| 0256973 | 2/1988 | European Pat. Off. . |
| 1156907 | 7/1969 | United Kingdom . |

*Primary Examiner*—Kim M. Lee
*Attorney, Agent, or Firm*—Horst M. Kasper

[57] ABSTRACT

The adjustable ankle brace of the present invention shown in FIGS. 1–7 is generally composed of a first sheet and of a second sheet. Such ankle brace can be also referred to as a spat and can be worn over a shoe or an athletic shoe. Overall, the ankle brace of the present invention is formed of a piece of flat material, where the flat material is fit over the foot or shoe such as to leave three openings when in place, namely a first opening for a heel, a second opening for the toes and a third opening for the shin of the leg. A completely disengageable zipper or fastener is provided between the second opening and the third opening such that after completely opening the zipper or fastener, the second opening and the third opening form a combined opening.

14 Claims, 8 Drawing Sheets

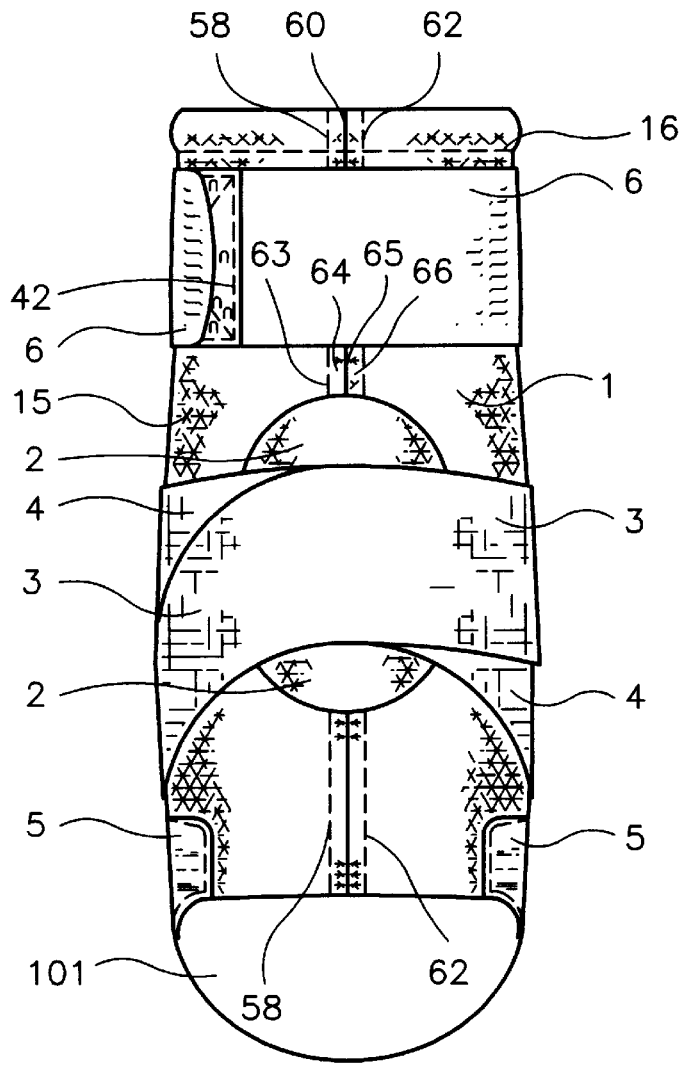
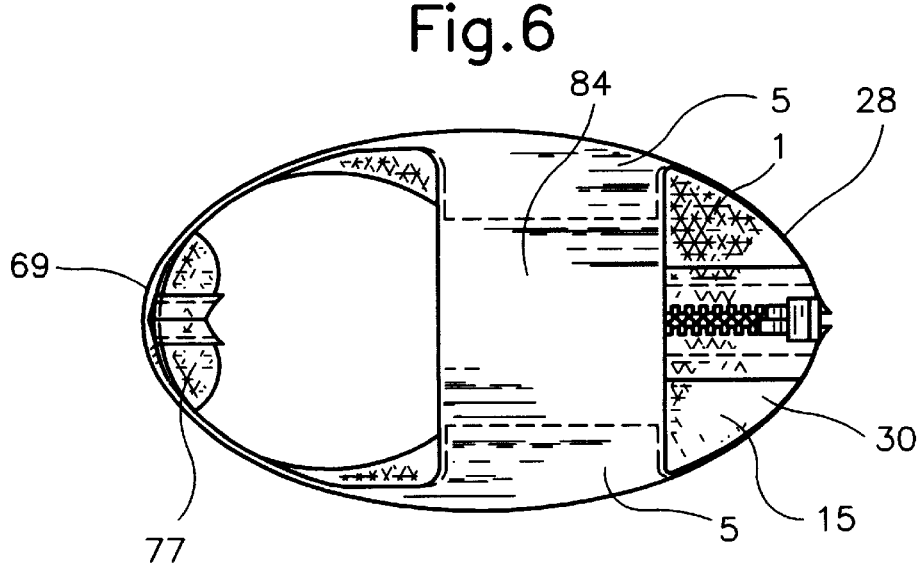
Fig.6
Fig.7

ADJUSTABLE ANKLE BRACE SYSTEM

BACKGROUND OF THE INVENTION

1. Field of the Invention

The invention relates to an ankle brace system to be worn on the outside of a shoe.

2. Brief Description of the Background of the Invention Including Prior Art

A foot and especially an ankle of a human being is a complex structure and at the same time an essential member used in many sporting activities. A foot can experience a variety of injuries such as strains, sprains, and fractures. In order to reduce the number of foot injuries, athletes attempt to protect the ankle, for example, by strengthening the ankle with tape. However, tape is inconvenient in certain aspects, since it is a cumbersome procedure to place and to remove the tape, since it takes time and patience to tape the foot, since the applied tape may shift after application of the tape, and since the fastening of the tape might not hold. In addition, the amount of tape required and thus the weight added to the foot and ankle can be substantial based on the overlapping of several layers of tape since one single layer of tape would not provide enough support to the ankle based on the relatively large elasticity of the tape. The removal of the tape and the therewith associated rolling up of the tape also requires time and patience.

L. H. Shaw in U.S. Pat. No. 958,896 teaches a method of making rands and of producing rand strips.

Tweedie in U.S. Pat. No. 1,153,977 teaches a boot top where a strap of patent leather or other suitable material connects the lower edges of the quarters across the arch of the foot.

Petri in U.S. Pat. No. 1,546,551 teaches an ankle brace, where forward-meeting edges of the casing are provided with straps and buckles to allow proper adjustment of the device. A similar strap and buckle extends from one side of the casing across to the other at its lower extremity.

Wharton in U.S. Pat. No. 1,730,400 teaches a stocking and shoe protector, where a cross-strap is adapted to extend across the shank portion of the shoe sole.

Cramer in U.S. Pat. No. 4,313,433 teaches an ankle stabilizer comprising a flexible jacket, a first strap, a second strap, a first fastener member associated with the first strap and a second fastener member associated with the second strap.

Vogelbach in U.S. Pat. No. 4,844,058 teaches a biomechanical ankle brace for treating an ankle. The brace has an elastic sleeve with a plurality of elastic strips secured to the sleeve. The sleeve is attached to a patient's ankle, and the elastic strips are wrapped around the ankle. The reference employs strips which are attached with hook and loop tape, such as Velcro.

Hoyt, Jr. in U.S. Pat. No. 4,908,960 teaches an overshoe which includes a sole section, a shoe section, and an ankle cover section having a flap. The flap is detachably secured in position by a fastener.

Krahenbuhl in U.S. Pat. No. 5,016,623 teaches an ankle support for use by persons recovering from an ankle injury. The ankle support includes a flexible heel foot support or shoe for fitting around the foot and ankle. A non-stretchable strap is fitted through a sleeve to pass over the outer ankle bone.

Cooper in U.S. Pat. No. 5,050,620 teaches an ankle brace with a stretchable, padded underliner which is open at the front to receive a wearer's foot and close therearound.

Hely in U.S. Pat. No. 5,067,486 teaches an ankle stabilizing appliance including a boot-like body member, and a pair of stabilizing straps which extend in opposite directions from the rear edge portions of the body member. The stabilizing straps are adapted to extend across and under the foot of the wearer, and then upwardly to a releasable attachment point on the side of the body member.

SUMMARY OF THE INVENTION

1. Purposes of the Invention

It is an object of the present invention to provide an adjustable ankle brace.

It is another object of the invention to provide an adjustable ankle brace, which is easy to use and convenient to apply and to remove.

It is a further object of the invention to provide an adjustable ankle brace, wherein the tightening is easily controlled, independent of a specific sport shoe over which the ankle support is applied and worn.

It is yet another object of the invention to provide an adjustable ankle brace which is flexible and can be easily maintained in a clean and attractive state.

These and other objects and advantages of the present invention will become evident from the description which follows.

2. Brief Description of the Invention

They adjustable ankle brace system of the present invention comprises an ankle support for placement over a shoe. A first sheet having an upper edge, a front edge, a rear edge and a bottom edge form a first side disposed over a shoe. A second sheet having an upper edge, a front edge, a rear edge and a bottom edge forming a second side disposed over a shoe and having attached the rear edge of the first sheet to the rear edge of the second sheet. A first fastener part is disposed along the front edge of the first sheet. A second fastener part is disposed along the front edge of the second sheet for engaging the first fastener part to securely attach the front edge of the first sheet to the front edge of the second sheet such that a third opening is formed along the upper edge of the first sheet and along the upper edge of the second sheet. An arch portion has a first end attached to the first sheet in an area of the bottom edge of the first sheet, and a second end attached to the second sheet in an area of the bottom edge of the second sheet, such that a first opening is formed between the arch portion and the rear edge of the first sheet attached to the rear edge of the second sheet, and such that a second opening is formed between the arch portion and the front edge of the first sheet securely attached to the front edge of the second sheet.

A cover piece can be attached in an area of the rear edge of the first sheet and of the rear edge the second sheet, and facing outwardly.

An upper strap can have a free end and an attached end disposed on and attached to the second sheet near the upper edge of the second sheet. Attachment means can be disposed on the upper strap near the free end of the upper strap such as to engage an outer surface of the upper strap upon pulling the upper strap around the first sheet and around the second sheet.

A first strap can be attached near the bottom edge to the first sheet, and positioned to form an angle of from about 10 to 30 degrees relative to a horizontal line of the first sheet, and wound around the first sheet and around the second sheet.

A first pulley can be disposed on the first sheet in an area of attachment of the first strap for being engaged by a free end of the first strap, for pulling the first strap tightly around the first sheet and the second sheet, and then closing the free end of the first strap around the first pulley.

A second strap can be attached near the bottom edge to the second sheet, and positioned to form an angle of from about 10 to 30 degrees relative to a horizontal line of the second sheet, and wound around the second sheet and around the first sheet.

A second pulley can be disposed on the second sheet in an area of attachment of the second strap for being engaged by a free end of the second strap, for pulling the second strap tightly around the second sheet and the first sheet, and then closing the free end of the second strap around the second pulley.

The arch portion can include a first elongated section attached to the first sheet in the area of the bottom edge of the first sheet, a bridge section attached to the first elongated section for being positioned under a shoe, and a second elongated section attached to the bridge section on a side of the bridge section disposed remote from the first elongated section. Said second elongated section can be attached to the bottom edge of the second sheet.

The first fastener part and the second fastener part can be furnished by a zipper, formed of two separate parts capable of engaging each other.

A short strap can be attached to the inside face of the second sheet and extending toward the front edge of the first sheet and having a third fastener part. Engagement means can be disposed on the inside of the first sheet for engaging and locking with the third fastener part.

An ankle support for placement over a shoe is made of a piece of flat material to be placed around a shoe from behind the shoe and having an upper edge, a first front edge, a second front edge, a first bottom edge, and a second bottom edge. Front fastening means are disposed at the first front edge and at the second front edge and are attached to the piece of flat material for releasably joining the first front edge to the second front edge. The closed front fastening means together with the upper edge defines a third opening. A bottom bridge includes a first elongated section, a bridge section, and a second elongated section, and is attached with the first elongated section to the first bottom edge and attached with the second elongated section to the second bottom edge. A first opening is defined by the bottom bridge and a rear part of the first bottom edge as well as with a rear part of the second bottom edge. A second opening is defined by the front fastening means, a front part of the first bottom edge, the bottom bridge and a front part of the second bottom edge.

An upper strap can be attached to the piece of flat material near to the upper edge and extend substantially parallel to the upper edge, with attachment means at an inner side of the upper strap and near a free end of the upper strap for attaching the free end of the upper strap to an outer side of the upper strap after placing the ankle support over a shoe and after winding the upper strap along the upper edge and around the leg.

A first and a second strap can be attached in the area of the elongated sections and near the bottom edges to the piece of flat material and extend from near a corner between the front edges and the bottom edges in a rearward and upward direction and having attachment means disposed at the free ends and outer side of the straps. A first and a second pulley can be attached to the piece of flat material in an area of attachment of the straps. Said pulleys extending horizontally such that the free ends of the straps are passed through openings furnished by the pulleys and then the free ends of the straps are attachable to the straps for forming a loop around the pulleys.

A method of attaching an ankle support comprises that a piece of flat material is placed from the rear over a shoe and foot with a foot portion solidly attached to a first bottom edge of the piece of flat material and to a second bottom edge of the piece of flat material such that the foot portion forms a bridge under the shoe. A first front edge and a second front edge of the piece of flat material are releasably attached to each other. An upper strap is wound around a leg near the upper edge of the piece of flat material. A free end of the upper strap is releasably attached to a surface area of the upper strap.

A first strap, attached near the first bottom edge to the piece of flat material and said first strap extending from near a corner between the first front edge and the first bottom edge, can be wound in a rearward and upward direction around the shoe. A free end of the first strap can be passed through a first pulley attached to the piece of flat material in an area of attachment of the first strap. Said first pulley extends horizontally such that the free end of the first strap is passed through an opening furnished by the first pulley. The free end of the first strap having attachment means, disposed at the free end and outside of the first strap, is attached to the first strap for forming a loop around the first pulley.

A second strap, attached near the second bottom edge to the piece of flat material, and said second strap extending from a corner between the second front edge and the second bottom edge, can be wound in a rearward and upward direction around the shoe. The free end of the second strap can be passed through a second pulley attached to the piece of flat material in an area of attachment of the second strap. Said second pulley extends horizontally such that the free end of the second strap is passed through an opening furnished by the second pulley. The free end of the second strap having attachment means, disposed at the free end and outside of the second strap, can be attached to the second strap for forming a loop around the second pulley.

Theoretical considerations indicate that a reinforcement of an ankle made of a long two-dimensional structure like a tape would be inferior to a three-dimensional structure adapted to strengthening and supporting the ankle.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention:

FIG. 6 is a rear view of the adjustable ankle brace shown in FIG. 1;

FIG. 7 is a bottom plan view of the adjustable ankle brace shown in FIG. 1;

DESCRIPTION OF INVENTION AND PREFERRED EMBODIMENT

Figure 1:
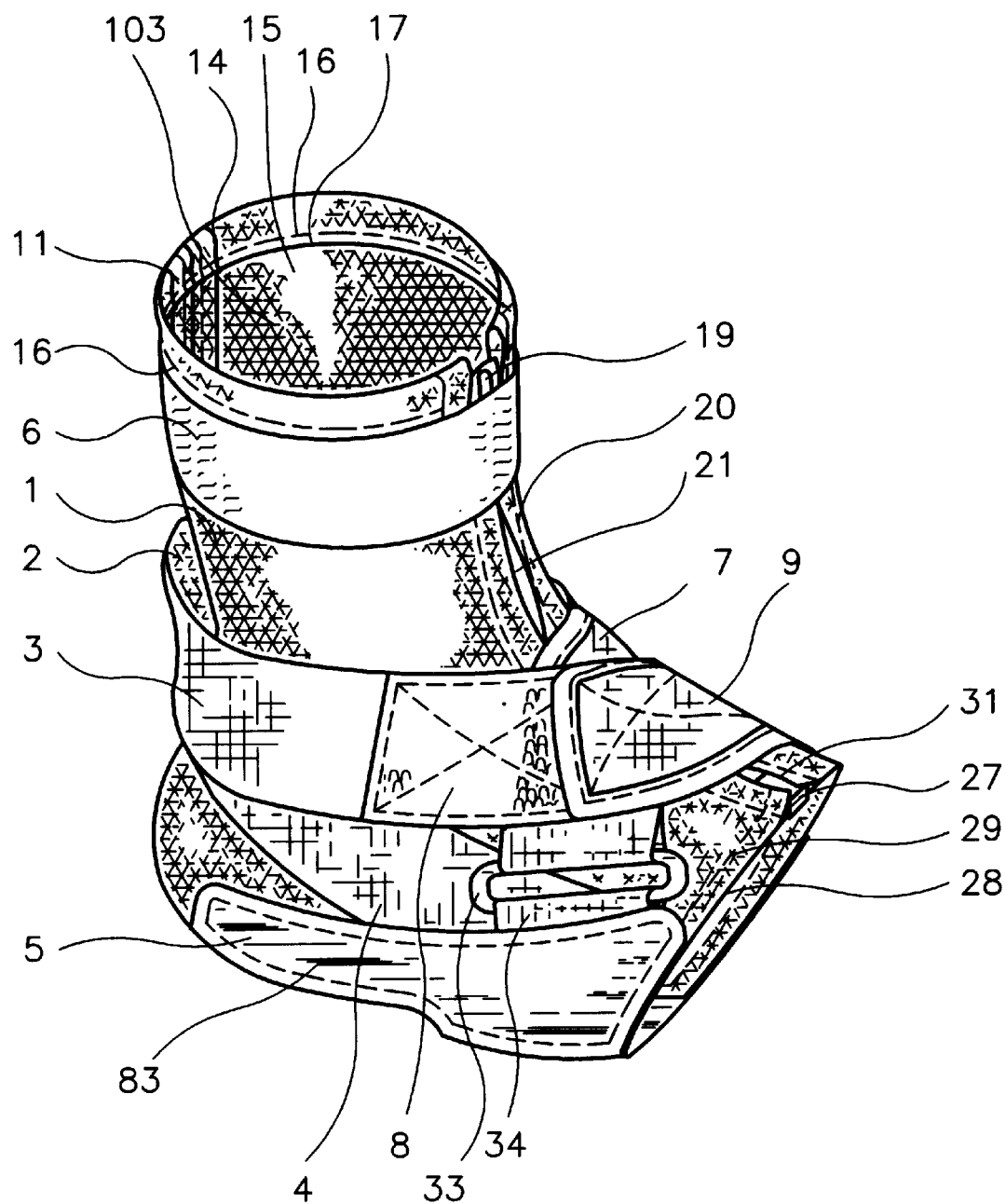
FIG. 1 is a front right hand perspective view of an adjustable ankle brace.
Figure 2:
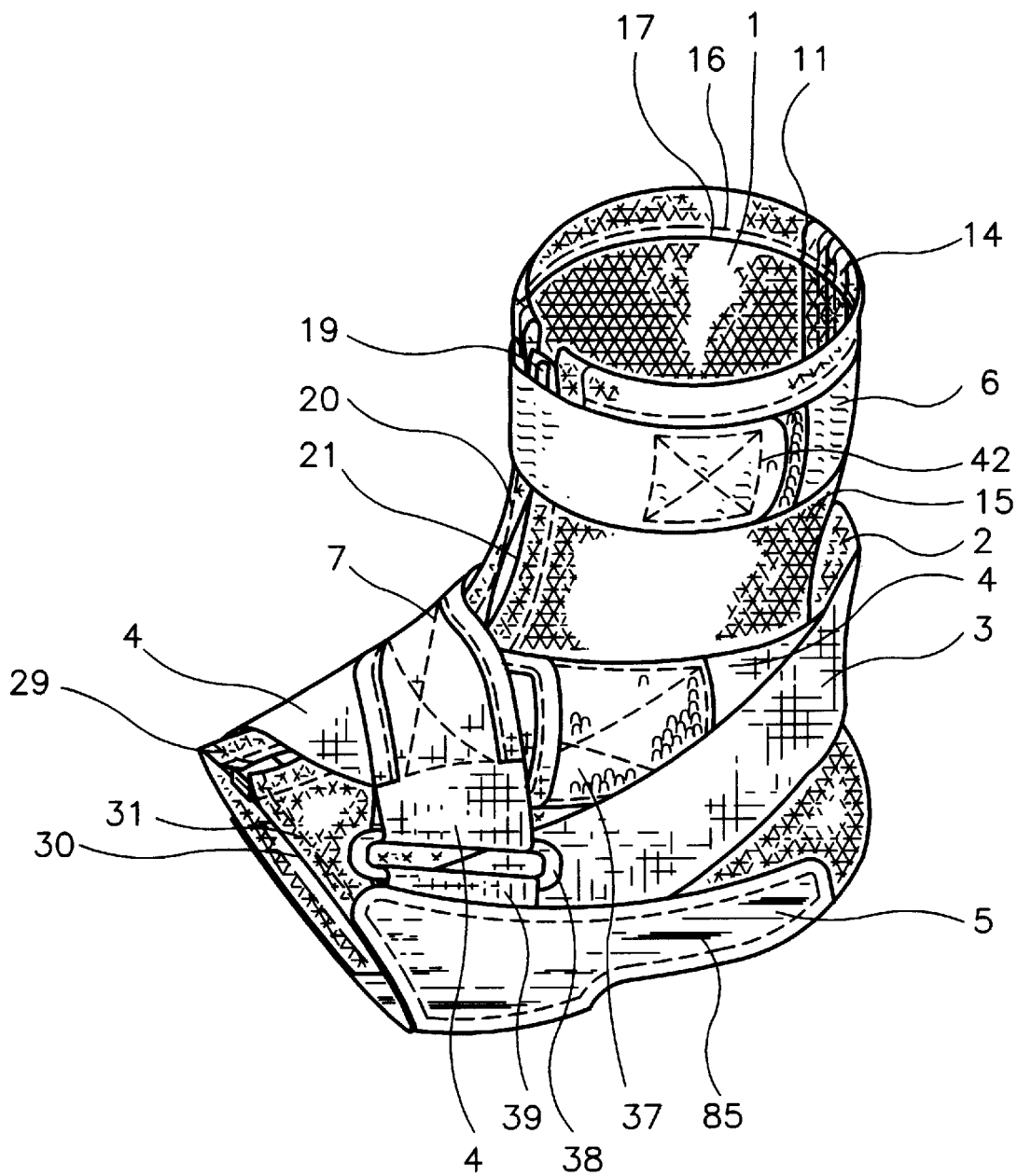
FIG. 2 is a front left hand perspective view of an adjustable ankle brace.

According to the present invention, there is provided for an adjustable ankle brace for the protection of the human ankle against injuries.

The adjustable ankle brace of the present invention shown in FIGS. 1–9 is generally composed of a first sheet 1 and of a second sheet 15. Such ankle brace can be also referred to as a spat and can be worn over a shoe or an athletic shoe. Overall, the ankle brace of the present invention is formed of a piece 100 (FIG. 8) of flat material, where the flat material is fit over the foot or shoe such as to leave three openings when in place, namely a first opening 101 (FIG. 6) for a heel, a second opening 102 (FIG. 5) for the toes and a third opening 103 (FIG. 1) for the shin of the leg. A completely disengageable zipper or fastener 19, 21 is provided between the second opening 102 and the third opening 103 such that after completely opening the zipper or fastener 19, 21, the second opening 102 and the third opening 103 form a combined opening.

Figure 5:
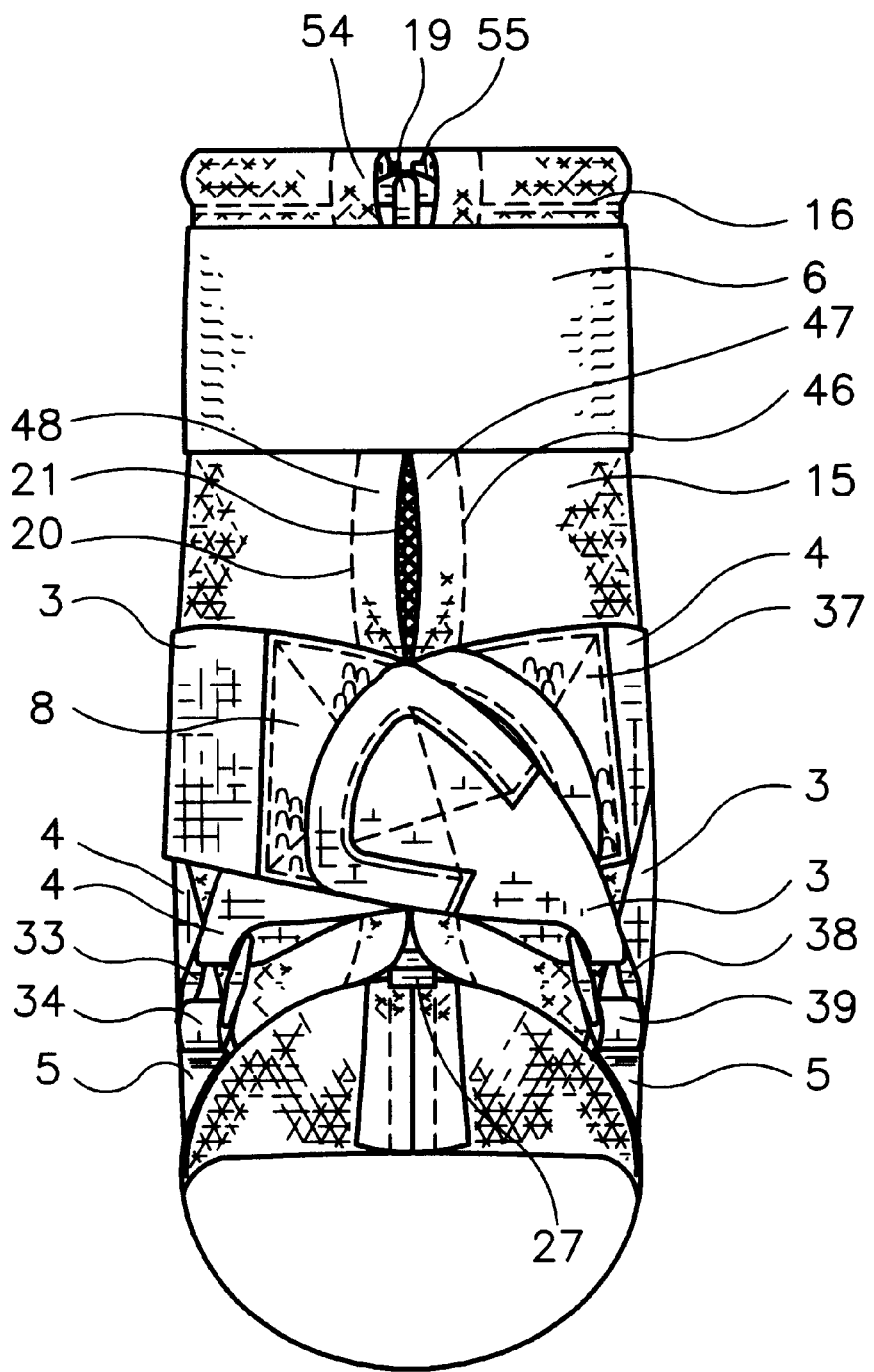
FIG. 5 is a front view of the adjustable ankle brace shown in FIG. 1.

The piece 100 of flat material is formed from a first sheet 1 and from a second sheet 15. The ankle brace for a right foot is a mirror image of an ankle brace for a left foot, where a mirror plane is placed between the right foot and the left foot. The drawings show and the following description will refer to an ankle brace for a right foot unless expressly stated otherwise. With reference to the right leg, the first sheet 1 of the ankle brace comes to be placed on the right outer side of a right shoe and the second sheet 15 comes to be placed on the outer left side of the right shoe. A first strap 4 is attached to the outside of the first sheet 1 and a second strap 3 is attached to the outside of the second sheet 15. The first sheet 1 and the second sheet 15 are joined at a rear seam, at a connecting line 60, running along an edge of the first sheet and along an edge of the second sheet and extending between the first opening 101 and the second opening 102. In a first approximation, the first sheet 1 and the second sheet 15 can be described as an epiped, where the upper straight edge corresponds to the upper rim 17 of the ankle brace, defining the third opening 103. The upper rim 17 is folded over and stitched along a seam 16. The width of the folded-over portion of the seam 16 is from 8 mm to 15 mm, and is preferably 10 mm. The first sheet 1 has a first front edge 47 to be disposed at the instep, and the second sheet 15 has a second front edge 48 to be disposed at the instep (FIG. 5). The first sheet 1 and the second sheet 15 are joined together along the first front edge 47 and along the second front edge 48 by means of a fastener 20. The shapes of the first front edge 47 and of the second front edge 48 are generally provided mirror symmetrical. The first sheet 1 has a lower first front edge 28, wherein the lower first front edge 28 is folded over and stitched along a seam 29. The second sheet 15 has a lower second front edge 30, wherein the lower first front edge 30 is folded over and stitched along a seam 31. The first sheet 1 has a first rear edge 11 to be disposed at the achilles, and the second sheet 15 has a second rear edge 14 to be disposed at the achilles. The first rear edge 11 is folded over and stitched along a seam 62 and the second rear edge 14 is folded over and stitched along a seam 58. The width of the folded-over portion of the seam 58, 62 is from 8 mm to 15 mm, and is preferably 10 mm. The shapes of the first rear edge 11 and of the second rear edge 14 are generally provided mirror symmetrical such that the rear edges can be stitched together in such a way that a smooth connection of the rear edges 11, 14 is furnished at the connecting line 60 of the first sheet 1 and the second sheet 15. As a result, the piece 100 (FIG. 8) of flat material furnished by the combined sheet of first sheet 1 and second sheet 15 is substantially mirror symmetrical in the rear edges 11, 14 which are sewn together.

Figure 9:
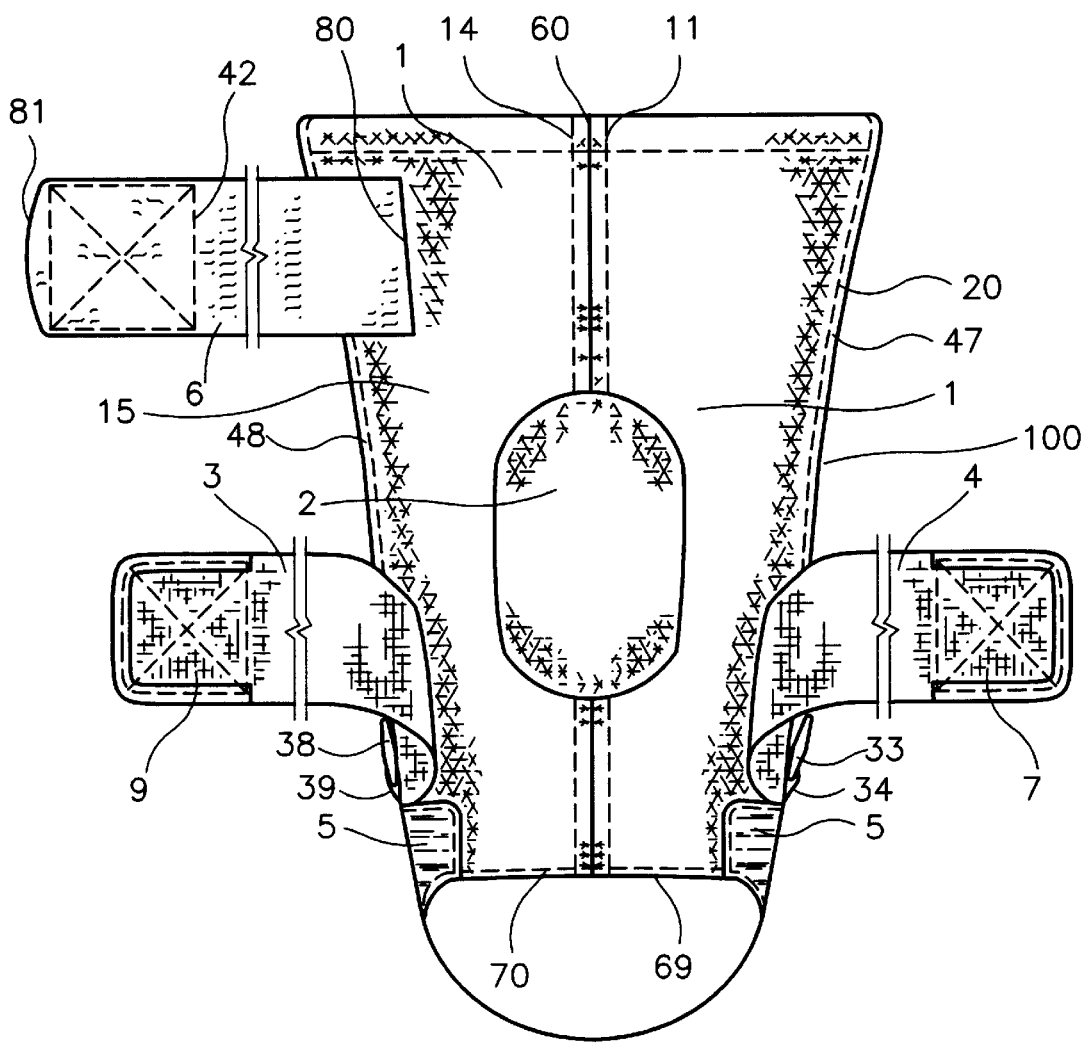
FIG. 9 is an rear elevational outside view on the rear surface of the adjustable ankle brace shown in FIG. 8.

The bottom rear edge 69 of the piece 100 of flat material is folded over and stitched along a seam 70 (FIG. 9). The width of the folded-over portion of the seam 70 is from 7 mm to 15 mm, and is preferably 8 mm.

Figure 8:
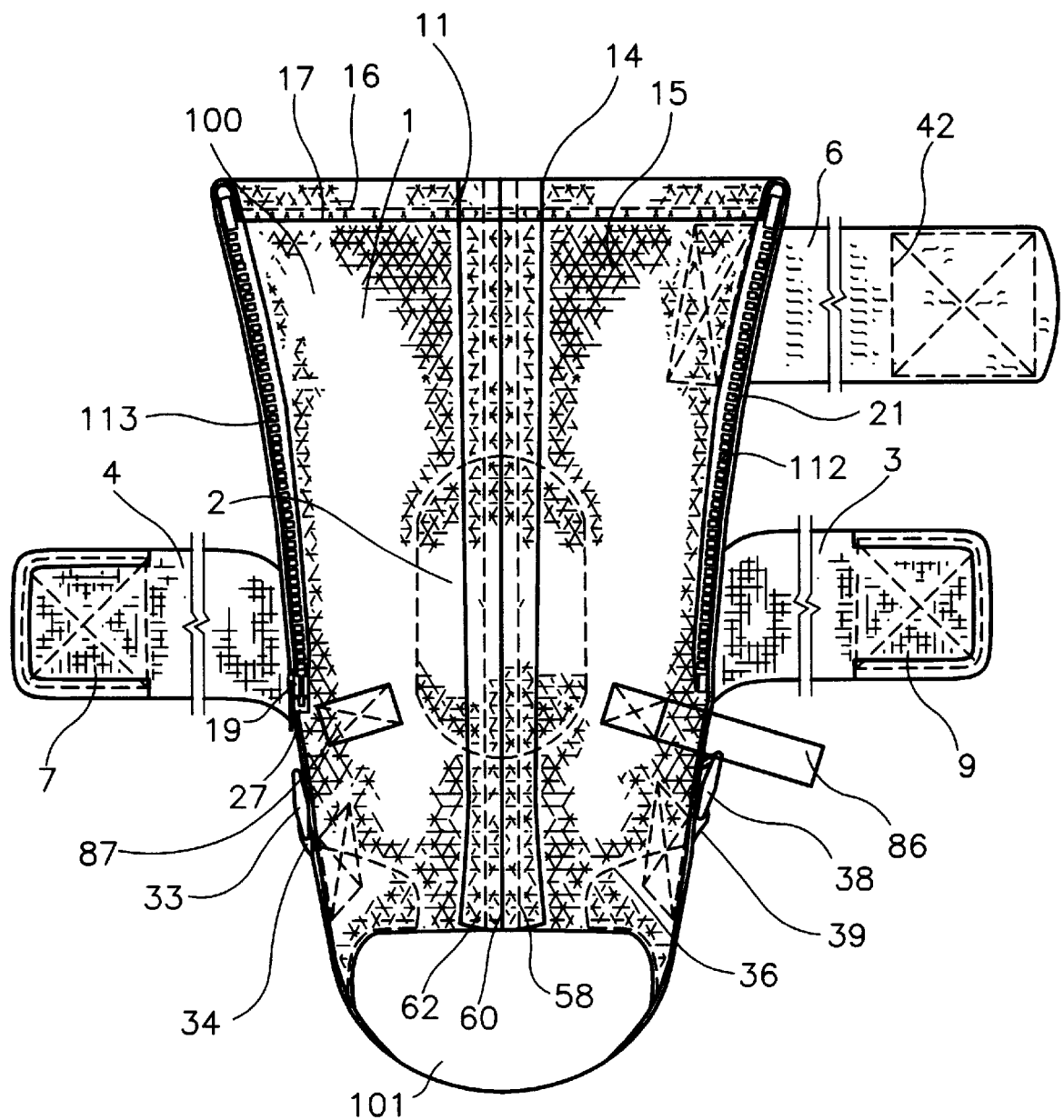
FIG. 8 is a front elevational view of the interior of an unfolded ankle brace shown in FIG. 1 in a released state.

According to a preferred embodiment, the first front edge 47 and the second front edge 48 (FIG. 9) are of approximately hyperbolic shape, wherein a first apex 113 of the first front edge 47 and a second apex 112 of the second front edge 48 FIG. 8 are located in the area where the largest curvature and the smallest radius of curvature is located on the upper front area of the foot. The hyperbolic shapes of the front edges 47, 48 are further adapted to provide at the upper end of the ankle brace, exhibiting the upper parts 54, 55 of the fastener 20, the third opening 103 of a proper size to surround the leg. Similarly, the lower end of the first front edge 47 and of the second front edge 48 are positioned such at the ankle brace, exhibiting the lower end 27 (FIG. 5) of the fastener 20, that the second opening 102 of a desired opening size for the front part of a shoe will result.

The length of the rear edges 11, 14 (FIG. 8) corresponds to the desired length of the covering of the rear part of the leg.

The adjustable ankle brace, wherein the rear edge 11 of the first sheet 1 and the rear edge 14 the second sheet 15 have been sewn together at a connecting line 60 (FIG. 6), is provided with a rear oval cover section 2 (FIG. 9), also called a cookie or a donut, disposed centered on the connecting line 60 and the rear oval cover section 2 is attached or sewn to the outside of the first sheet 1 and of the second sheet 15. The rear oval cover section 2 is sewn to the assembled and joined first sheet 1 and second sheet 15 at a height-level to cover the achilles. The rear cover section 2 is to provide further protection for the achilles.

The second sheet 15 (FIGS. 8 and 9) is furnished with a upper strap 6 made of fabric, having a surface with loops on one side of the elastic strap, and wherein the material with the loops is sold under the trademark VELCRO. The loops are on that side of the upper strap 6 which is outwardly disposed when placed around the rear area of the ankle brace. The upper strap 6 is sewn at a first end 80 of the upper strap 6 to the second sheet 15 in the area of the second front edge 48 near the upper rim 17 of the ankle brace. The upper strap 6 is positioned so as to surround the ankle brace along a substantially horizontal path. The looped surface of the strap 6 is facing outwardly at the plane of connection of the upper strap 6 to the second sheet 15. A corresponding hook-like filament strap section 42 is sewn at a second end 81 (FIG. 9) of the upper strap 6 to the inner side of the upper strap 6 to engage the loop-like fabric surface of the upper strap 6 when the upper strap 6 is wound around the ankle brace and leg and for tightening the upper strap 6. Preferably, the second end 81 of the upper strap 6 is formed rounded at the two corners. The length of the upper strap 6 is such as to wind from about 1 to 2 times, and preferably from about 1.2 to 1.6 times, around the upper end of the ankle brace placed around a leg. The width of the upper strap 6 can be from about 0.1 to 0.3 times the length of the rear edges 11, 14 of the first sheet 1 and the second sheet 15, and is preferably from about 0.15 to 0.25 of the length of the rear edges 11, 14. The upper strap 6 is made of a material which is slightly elastic and extends by up to about 25% of its length elastically when subjected to pulling forces.

Figure 3:
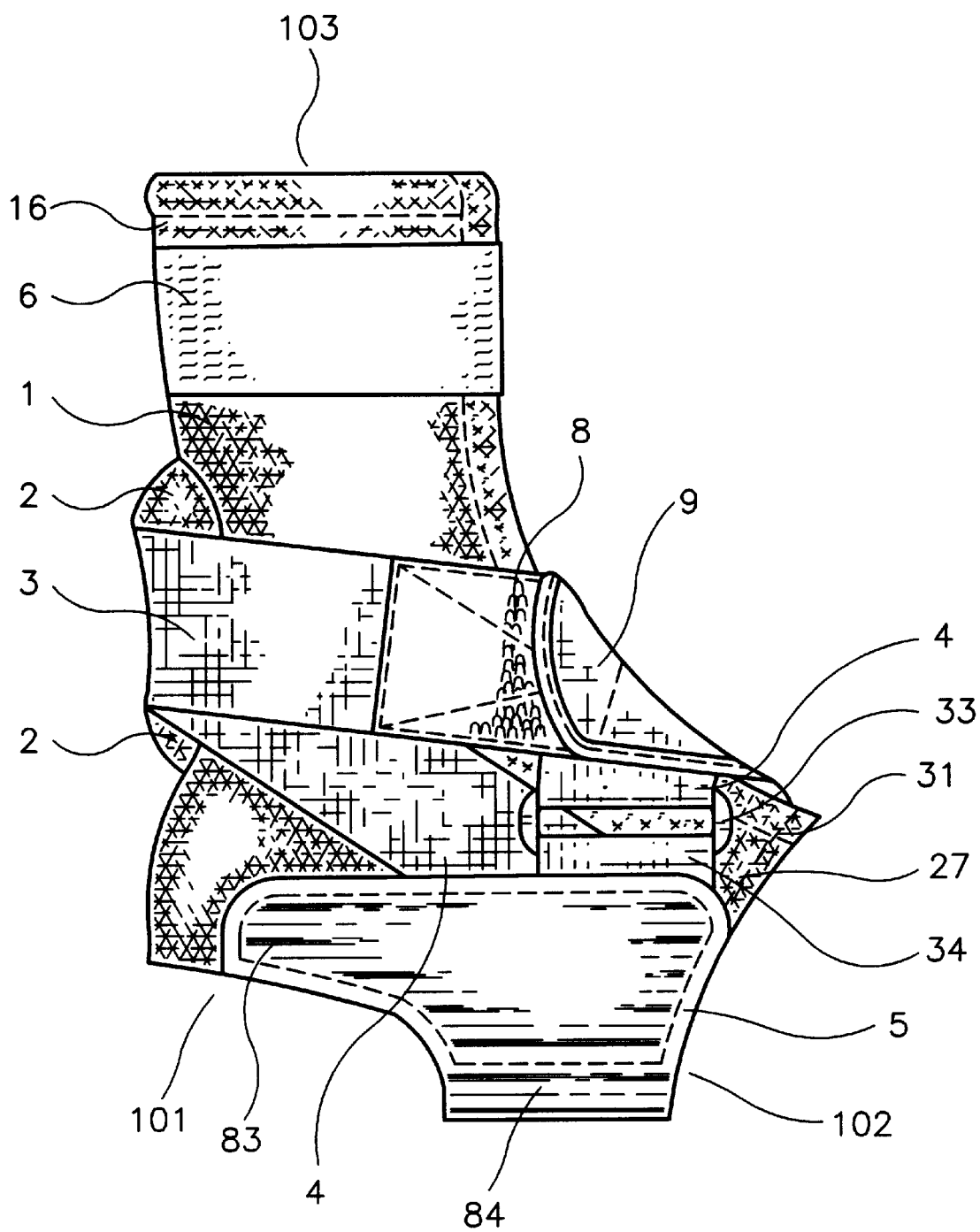
FIG. 3 is a right side view of the adjustable ankle brace shown in FIG. 1.
Figure 4:
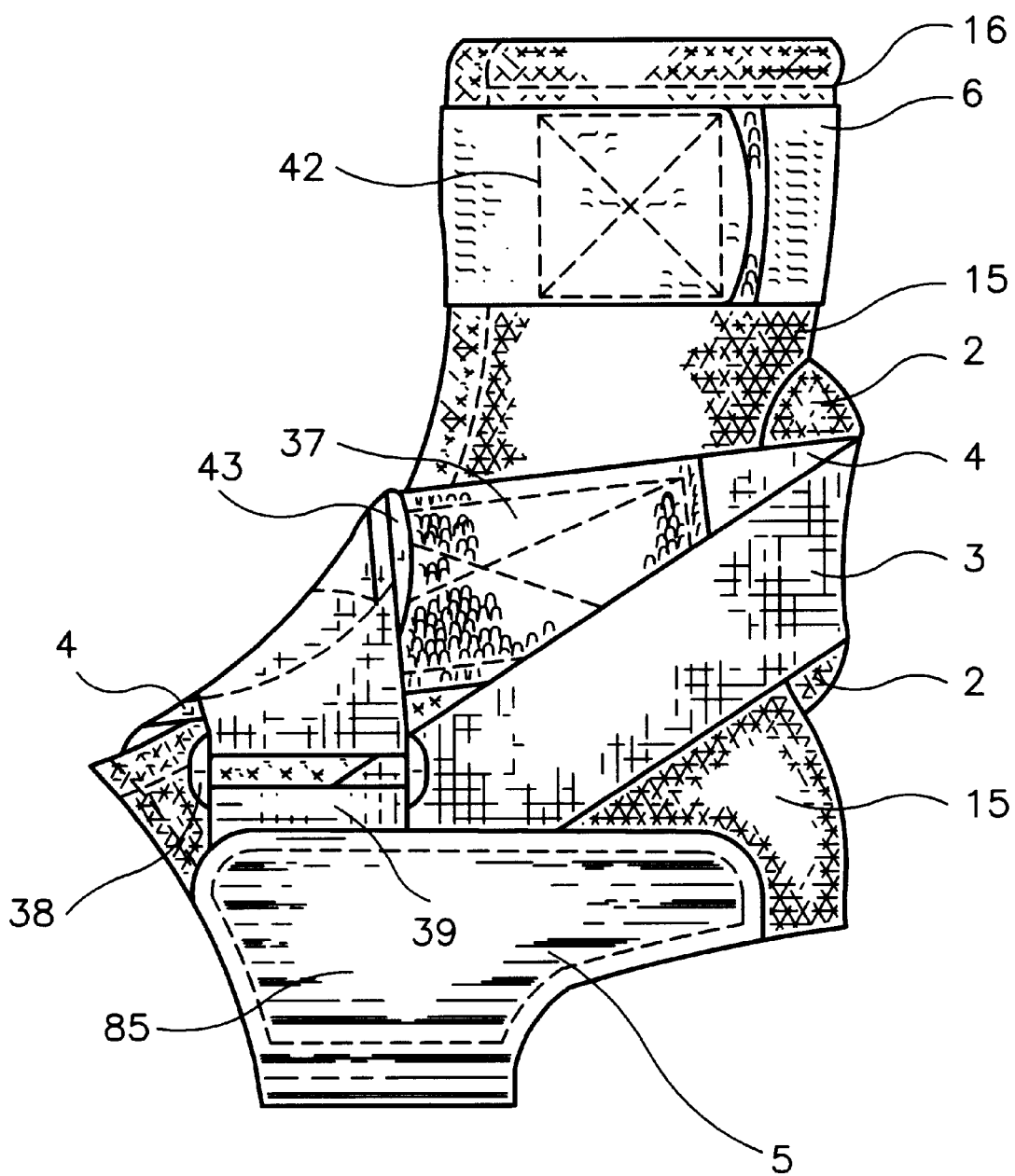
FIG. 4 is a left side view of the adjustable ankle brace shown in FIG. 1.

The piece 100 further includes an arch portion 5 (FIGS. 3 and 4). The first sheet 1 and the second sheet 15 are connected together with an arch portion 5 sewn to bottom edges of the first sheet 1 and the second sheet 15. The arch portion 5 is disposed on the outside of the respective sheet and under the respective shoe or foot. The arch portion 5 is disposed such that the cover the central areas of the respective sheets and provide additional strength and stiffness. The arch portion 5 (FIGS. 3 and 4) is attached with a first end to the lower end and at the outside of the first sheet 1 and with a second end to the lower end and at the outside of the second sheet. The arch portion 5 is generally composed of a first elongated section 83 solidly attached to the outside of the lower part of the first sheet 1, a bridge section 84 and a second elongated section 85 to be attached to the lower end and outside of the second sheet 15. The first elongated section 83 (FIG. 3) extends on the first sheet 1 from about the lower front edge and the second opening 102 at a point projected by the front end of the rear oval cover section 2 and the first opening 101.

As shown in FIG. 3, a first pulley 33 is attached at the outer side of the first sheet 1 near the arch portion 5 and the front end, i.e. the second opening 102, of the first sheet 1. The pulley 33 comprises two approximately parallel rods or bars with a curved cross-section to reduce friction. The two rods or bars are held together at their ends by respective junction sections. A first one of the rods or bars is held by a first loop 34 of a heavy-duty elastic tape material, such as cloth made of plastic fibers, where the loop 34 is generated by folding a length of tape material over the first rod or bar and then sewing the two end parts of the looped tape material between the first sheet 1 and the first elongated section 83 of the arch portion 5. The bars or rods are generally oriented parallel to the first elongated section 83 of the arch portion 5.

As shown in FIG. 4, a second pulley 38 is attached at the outer side of the second sheet 15 near the arch portion 5 and the front end, i.e. the second opening 102, of the second sheet 15. The second pulley 38 and a second loop 39 are constructed correspondingly as are the first pulley 33 and the first loop 34. However, the ends of the folded second loop 39 is sewn between the second elongated section 85 of the arch portion 5 and the second sheet 15.

As shown in FIG. 3, the first strap 4 is attached with a first end to the first sheet 1 in the area of the attachment of the first loop 34 with the first pulley 33. Similar to the upper strap 6, one side of the first strap 4 is provided with a looped surface. The first strap 4 is provided at a free end and on the same side as the looped surface of the first strap 4 with a fabric strip face 7 with hooks (FIGS. 8, 9). A looped fabric surface 37 is furnished in an area of the middle along the length of the first strap 4 on the same surface side of the first strap 4 as the fabric strip face 7 with hooks. The first strap 4 is used by entering the free end of the first strap through the first pulley 33. Then, when wearing the ankle brace, the fabric strip face 7 engages with the looped surface of the first strap 4. The free end of the first strap 4 having the fabric strip face 7 with hooks at the free end of the first strap 4 is slipped through the first pulley 33, from the inner side of the pulley disposed toward the foot, and the free end is looped around the first pulley 33 such that the fabric strip face 7 with hooks can engage with the looped surface or looped fabric surface 37 of the first strap 4, in an area where the looped surface of the first strap 4 was not yet pulled through the first pulley 33, but is already disposed near the first pulley 33. The length of the first strap 4 is furnished such that, upon assembly around the shoe and foot, the engagement of the fabric strip face 7 with hooks and of the looped surface of the first strap 4 occurs near the position of the first pulley 33. Alternatively, the length of the first strap 4 can be from about 30 to 60 centimeters, and is preferably between 40 and 50 centimeters. The first strap 4 is preferably made of a strong fabric material resistant to elastic stretching to provide firm bracing support. The width of the first strap 4 can be from about 2 to 8 centimeters, and is preferably from about 3 to 5 centimeters. The first strap 4 is preferably disposed at an angle of from about 20 to 50 degrees relative to a line parallel to the rod or bar of the pulley 33.

As can be seen in FIG. 4, a second strap 3 is attached to the second sheet 15 in the area of the attachment of the second loop 39 with the second pulley 38 at the opposite side of the ankle brace where the first strap 4 is attached. Similar to the first strap 4, one side of the second strap 3 is provided with a looped surface. The second strap 3 is provided at a free end and on the same side as the looped surface of the first strap 3 with a fabric strip face 9 with hooks (FIGS. 8, 9). A looped fabric surface 8 is furnished in an area of the middle along the length of the second strap 3 on the same surface side of the second strap 4 as the fabric strip face 9 with hooks. When wearing the ankle brace, the fabric strip face 9 engages with the looped surface of the second strap 3, in that the free end with the fabric strip face 9 with hooks of the second strap 3 is slipped through the second pulley 38, from the inner side disposed toward the foot, and is looped around the second pulley 38 such that the fabric strip face 9 with hooks can engage with the looped fabric surface 8 of the second strap 3, where the looped fabric surface 8 of the second strap 3 was not pulled through the second pulley 38, but is disposed near the second pulley 38. The length of the second strap 3 is furnished such that, upon assembly around the shoe and foot, the engagement of the fabric strip face 9 with hooks and of the looped fabric surface 8 of the second strap 3 occurs near the position of the second pulley 38. The length and the width of the second strap 3 corresponds to the length and the width of the first strap 4. The second strap 3 is preferably made of the same strong fabric material substantially resistant to elastic stretching as the first strap 4. The second strap 3 is preferably disposed at an angle of from about 20 to 50 degrees relative to a line parallel to the rod or bar of the pulley 38.

As can be seen on FIG. 8, a fourth strap 86 is sewn to the inside of the second sheet 15 in the area of the instep. The fourth strap 86 is provided with a looped surface on the side facing outwardly. A fabric strip face 87 is sewn to the inside of the first sheet 1 in the area of the instep. The fabric strip face 87 is provided with hooks, wherein the hooks of the fabric strip face 87 are to engage with the looped surfaces of the third strap 86 when the ankle support is being worn.

The sheets 1 and 15 are preferably provided by a plastic material, in particular polyester foam with nylon backing on two sides having a thickness of from about 0.2 to 0.5 millimeters and preferably from about 0.25 to 0.4 millimeters such as commercially available under the trademark Neoprene 1400.

The first strap 1 and the second strap 15 are made from non-stretch loop polyester and from non-stretch hook polyester commercially available under the tradename Velcrostraps. The width of the first strap 1 and of the second strap 15 can be preferably from about 4 to 6 centimeters.

The third upper strap 6 is made out of a strong band made of plastic such as a composite of nylon and polyester and having loops of a Velcro fastener, such as commercially available under the trademark Velstretch. The width of the third upper strap can be preferably from about 4 to 6 centimeters.

The pulleys 33 and 38 are teflon pulleys. The loops 34 and 39 are heavy duty elastic and preferably include materials such as rubber and nylon. The width of the loops 33 and 38 can be preferably from about 4 to 6 centimeters.

The arch portion 5 is made out of bladder cloth or of a strong fabric coated with a plastic cover on both sides.

The ankle brace is operated as follows: The bridge portion 84 of the arch portion 5 is placed under a shoe to be covered. Then, the piece comprising first sheet 1 and second sheet 15 is placed around the shoe. The fabric strip face 87 of the first sheet 1 is pressed onto the fourth strap 86 of the second sheet 15 in order to keep the front edges 47 and 48 together. The front edges 47, 48 are then closed by means of the fastener 20. The third upper strap 6 is wound around the upper part of the ankle brace and, after adjustment for a tight but comfortable fit, attached with the fabric strip face 42 with hooks (FIG. 8) to the looped surface of the third upper strap 6. Then, the first strap 4 is wound, first behind the achilles, around the ankle brace, passed through the first pulley 33, pulled tight, and fastened by pressing the fabric strip face 7 with hooks onto the looped surface of the first strap 4. Then the second strap 3 is wound, first behind the achilles and crossing over the first strap 4, around the ankle brace and in a sense opposite to the first strap 4, then passed through the second pulley 38, and then the second strap 3 is tightened and fastened by pressing the fabric strip face 9 with hooks onto the looped surface of the second strap 3.

It will be understood that each of the elements described above, or two or more together, may also find a useful application in other types of ankle braces differing from the types described above.

While the invention has been illustrated and described as embodied in the context of an adjustable ankle brace with straps, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An ankle support for placement over a shoe comprising
   a first sheet having an upper edge, a front edge, a rear edge and a bottom edge for forming a first side disposed over a shoe;
   a second sheet having an upper edge, a front edge, a rear edge and a bottom edge for forming a second side disposed over a shoe and said second sheet having attached the rear edge of the first sheet to the rear edge of the second sheet;
   a first fastener part disposed along the front edge of the first sheet;
   a second fastener part disposed along the front edge of the second sheet for engaging the first fastener part to securely attach the front edge of the first sheet to the front edge of the second sheet such that a third opening is formed along the upper edge of the first sheet and along the upper edge of the second sheet;
   an arch portion having a first end attached to the first sheet in an area of the bottom edge of the first sheet, and having a second end attached to the second sheet in an area of the bottom edge of the second sheet, such that a first opening is formed between the arch portion and the rear edge of the first sheet attached to the rear edge of the second sheet, and such that a second opening is formed between the arch portion and the front edge of the first sheet securely attached to the front edge of the second sheet; wherein the arch portion includes a first elongated section attached to the first sheet in the area of the bottom edge of the first sheet, a bridge section attached to the first elongated section for being positioned under a shoe, and a second elongated section attached to the bridge section on a side of the bridge section disposed remote from the first elongated section, and wherein said second elongated section is attached to the bottom edge of the second sheet.

2. The ankle support according to claim 1, further comprising
   a cover piece attached in an area of the rear edge of the first sheet and of the rear edge of the second sheet, and facing outwardly.

3. The ankle support according to claim 1, further comprising
   an upper strap having a free end and an attached end disposed on and attached to the second sheet near the upper edge of the second sheet;
   attachment means disposed on the upper strap near the free end of the upper strap such as to engage an outer surface of the upper strap upon pulling the upper strap around the first sheet and around the second sheet.

4. The ankle support according to claim 1, further comprising
   a first strap attached near the bottom edge to the first sheet, and positioned to form an angle of from about 10 to 30 degrees relative to a horizontal line of the first sheet, and wound around the first sheet and around the second sheet.

5. The ankle support according to claim 4, further comprising
   a first pulley disposed on the first sheet in an area of attachment of the first strap for being engaged by a free end of the first strap, for pulling the first strap tightly around the first sheet and the second sheet, and then closing the free end of the first strap around the first pulley.

6. The ankle support according to claim 1, further comprising
   a second strap attached near the bottom edge to the second sheet, and positioned to form an angle of from about 10 to 30 degrees relative to a horizontal line of the second sheet, and wound around the second sheet and around the first sheet.

7. The ankle support according to claim 6, further comprising
   a second pulley disposed on the second sheet in an area of attachment of the second strap for being engaged by a free end of the second strap, for pulling the second strap tightly around the second sheet and the first sheet, and then closing the free end of the second strap around the second pulley.

8. The ankle support according to claim 1, wherein the first fastener part and the second fastener part are furnished by a zipper, formed of two separate parts capable of engaging each other.

9. The ankle support according to claim 1, further comprising a short strap attached to an inside face of the second sheet and extending toward the front edge of the first sheet and having a third fastener part;

engagement means disposed on the inside of the first sheet for engaging and locking with the third fastener part.

10. An ankle support for placement over a shoe, comprising a piece of flat material to be placed around a shoe from behind the shoe and having an upper edge, a first front edge, a second front edge, a first bottom edge, and a second bottom edge, front fastening means disposed at the first front edge and at the second front edge and attached to the piece of flat material for releasably joining the first front edge to the second front edge, wherein the front fastening means in a closed position together with the upper edge defines a third opening;

a bottom bridge including a first elongated section, a bridge section, and a second elongated section, and attached with the first elongated section to the first bottom edge and attached with the second elongated section to the second bottom edge, wherein a first opening is defined by the bottom bridge and a rear part of the first bottom edge as well as with a rear part of the second bottom edge, and wherein a second opening is defined by the front fastening means, a front part of the first bottom edge, the bottom bridge and a front part of the second bottom edge.

11. The ankle support according to claim 10, further comprising an upper strap attached to the piece of flat material near to the upper edge and extending substantially parallel to the upper edge, with attachment means at an inner side of the upper strap and near a free end of the upper strap for attaching the free end of the upper strap to an outer side of the upper strap after placing the ankle support over a shoe and after winding the upper strap along the upper edge and around the leg.

12. The ankle support according to claim 10, further comprising a first strap attached in an area of the first elongated section and near the first bottom edge to the piece of flat material and extending from near a corner between the first front edge and the first bottom edge in a rearward and upward direction and having attachment means disposed at a free end and outer side of the first strap;

a first pulley attached to the piece of flat material in an area of attachment of the first strap, and said first pulley extending horizontally such that the free end of the first strap is passed through an opening furnished by the first pulley and then the free end of the first strap is attachable to the first strap for forming a loop around the first pulley.

13. The ankle support according to claim 10, further comprising a second strap attached in an area of the second elongated section and near the second bottom edge to the piece of flat material and extending from near a corner between the second front edge and second bottom edge in a rearward and upward direction and having attachment means disposed at a free end and outside of the second strap;

a second pulley attached to the piece of flat material in an area of attachment of the second strap, and said second pulley extending horizontally such that the free end of the second strap is passed through an opening furnished by the second pulley and then the free end of the second strap is attachable to the second strap for forming a loop around the second pulley.

14. An ankle support for placement over a shoe comprising a first sheet having an upper edge, a front edge, a rear edge and a bottom edge for forming a first side disposed over a shoe;

a second sheet having an upper edge, a front edge, a rear edge and a bottom edge for forming a second side disposed over a shoe and said second sheet having attached the rear edge of the first sheet to the rear edge of the second sheet;

a first zipper part disposed along the front edge of the first sheet;

a second zipper part disposed along the front edge of the second sheet for engaging the first zipper part to securely attach the front edge of the first sheet to the front edge of the second sheet such that a third opening is formed along the upper edge of the first sheet and along the upper edge of the second sheet;

an arch portion having a first end fixedly attached to the first sheet in an area of the bottom edge of the first sheet, and having a second end fixedly attached to the second sheet in an area of the bottom edge of the second sheet, such that a first opening is formed between the arch portion and the rear edge of the first sheet attached to the rear edge of the second sheet, and such that a second opening is formed between the arch portion and the front edge of the first sheet securely attached to the front edge of the second sheet; wherein the arch portion includes a first elongated section attached to the first sheet in the area of the bottom edge of the first sheet, a bridge section attached to the first elongated section for being positioned under a shoe, and a second elongated section attached to the bridge section on a side of the bridge section disposed remote from the first elongated section, and wherein said second elongated section is attached to the bottom edge of the second sheet.

\* \* \* \* \*